United States Patent [19]
Brodkin et al.

[11] Patent Number: 6,086,662
[45] Date of Patent: Jul. 11, 2000

[54] LOW FUSING DENTAL PORCELAINS CONTAINING TETRAGONAL RUBIDIUM-LEUCITE

[75] Inventors: Dmitri Brodkin, West Orange; Carlino Panzera, BelleMead, both of N.J.

[73] Assignee: Jeneric/Pentron Incorporated, Wallingford, Conn.

[21] Appl. No.: 09/168,544

[22] Filed: Oct. 8, 1998

Related U.S. Application Data

[60] Provisional application No. 60/062,376, Oct. 15, 1997.

[51] Int. Cl.$^7$ .................. C03C 10/10; A61C 13/083; A61C 13/00
[52] U.S. Cl. ............... 106/35; 433/202.1; 433/201.1; 501/6; 501/32; 501/59; 501/66; 501/70; 501/72; 501/74; 264/16
[58] Field of Search .................. 106/35; 501/6, 501/32, 59, 66, 70, 72, 74; 433/202.1, 201.1; 264/16

[56] References Cited

U.S. PATENT DOCUMENTS

| | | | |
|---|---|---|---|
| 3,052,982 | 9/1962 | Weinstein et al. | 32/8 |
| 3,236,662 | 2/1966 | MacDowell | 106/39 |
| 4,455,383 | 6/1984 | Panzera | 501/6 |
| 4,550,030 | 10/1985 | Ohi et al. | 106/35 |
| 4,604,366 | 8/1986 | Kacicz et al. | 501/6 |
| 4,798,536 | 1/1989 | Katz | 433/212.1 |
| 5,192,722 | 3/1993 | Bedard et al. | 501/128 |
| 5,614,330 | 3/1997 | Panzera et al. | 428/697 |
| 5,994,246 | 11/1999 | Denry | 501/32 |

FOREIGN PATENT DOCUMENTS 0 543 065   5/1993   European Pat. Off. .

OTHER PUBLICATIONS

Denry IL, Holloway JA, Rosenstiel SF; Effect of Ion Exchange on the Microstructure, Strength, and Thermal Expansion Behavior of a Leucite–reinforced Porcelain; Journal of Dental Research 77(4), 583–588, Apr. 1998.

Martin RF, Lagache M; Cell Edges and Infrared Spectra of Synthetic Leucites and Pollucites in the System $KAlSi_2O_6$—$RbAlSi_2O_6$—$CsAlSi_2O_6$; Canadian Mineralogist vol. 13, pp. 275–281 (1975). No month.

Taylor D; Thermal Expansion Data XV, Complex Oxides with the Leucite Structure and Frameworks Based on Six–Membered Rings of Tetrahedra; Journal, vol. 90, No. 6, 197–204, 1991. No month.

Taylor D, Henderson CMB; The Thermal Expansion of the Leucite Group of Minerals; The American Mineralogist, vol. 53, 1476–1489, Sep.–Oct., 1968.

*Primary Examiner*—C. Melissa Koslow
*Attorney, Agent, or Firm*—Ann M. Knab

[57] ABSTRACT

A dental porcelain composition, comprising a glassy matrix and rubidium leucite crystallites embedded therein, and having maturing temperatures in the range from about 650° C. to about 800° C. and CTEs in the range from about 13 to about 17, more preferably in the range from about 13.5 to about 16, and most preferably in the range from about 14 to about $16 \times 10^{-6}$/° C. (measured from 25° C. to 400° C.). The tetragonal rubidium leucite is preferably both fine-grained (i.e., having average diameters of less than about 5 microns) and uniformly sized. Preferably, the average diameters are less than about 1 to about 2 microns.

18 Claims, 3 Drawing Sheets

LOW FUSING DENTAL PORCELAINS CONTAINING TETRAGONAL RUBIDIUM-LEUCITE

CROSS-REFERENCE TO RELATED APPLICATIONS

This application claims priority to U.S. Provisional Application Ser. No. 60/062,376, filed Oct. 15, 1997 which is hereby incorporated by reference.

BACKGROUND OF THE INVENTION

1. Field of the Invention

The present invention relates to tetragonal rubidium leucite-containing dental porcelain compositions for dental restorations. More particularly, this invention relates to low-fusing dental porcelain compositions useful in the preparation and repair of dental restorations such as porcelain-fused-to-metal restorations, all-ceramic restorations, inlays, onlays and veneers, wherein the leucite is fine-grained.

2. Brief Description of the Related Art

Porcelain dental restorations, such as crowns, bridges, and the like are highly favored because the porcelains provide strength, wear resistance, and favorable aesthetics. Older porcelain restorations generally comprise at least one porcelain layer on a metal framework, commonly known as porcelain-fused-to-metal ("PFM") restorations. Typically, PFM restorations are fabricated by applying a dental porcelain powder in aqueous slurry to a metal alloy framework, then firing the porcelain at high temperature to form a tight, impervious porcelain layer having the appearance of natural dentition. Those skilled in the art recognize that it is important that the firing temperature of the porcelain be at least 100° C. below the solidus temperature of the alloy used as the metal framework, to prevent distortion of the metal framework. It is further important that the coefficient of thermal expansion (CTE) of the porcelain be only slightly less than that of the metal so that no cracks are produced in the porcelain layer due to thermal expansion mismatch stress occurring during firing and cooling down. Metal alloys heretofore employed in the manufacture of dental restorations have typically possessed moderately high coefficients of thermal expansion ranging from about $13 \times 10^{-6}$/° C. to about $17.5 \times 10^{-6}$/° C., with the exception of titanium, which has a coefficient of thermal expansion of about $9 \times 10^{-6}$/° C.

In commonly assigned U.S. application Ser. No. 08/532,179 filed Sep. 22, 1995, now abandoned, the contents of which are incorporated by reference herein, a dental porcelain composition is described which is amorphous, i.e., single phase, and which possesses a moderately high coefficient of thermal expansion closely matching those of conventional alloys and some ceramics heretofore employed in the manufacture of dental restorations. This composition is advantageously applied to such conventional alloys to provide an extremely smooth, glassy surface on the resulting dental restoration.

Newer restorations, however, generally comprise a ceramic core in place of the traditional metal, with at least one additional porcelain layer. These are commonly referred to as "all-ceramic" systems, and can provide even better aesthetics than the metal-porcelain systems. Among all-ceramic systems, high strength porcelains provide a more natural translucency and therefore much improved aesthetics. Dental ceramics exhibit a wide range of coefficients of thermal expansion, from as low as about $8 \times 10^{-6}$/° C. (e.g., alumina) to as high as about $18 \times 10^{-6}$/° C. (e.g., some leucite-reinforced ceramics).

Among the commercially available all-ceramic systems, many are based on pressable, high-strength feldspathic porcelains, for example pressable leucite-reinforced porcelains commercially available under the trade name "OPC®" from Jeneric®/Pentron®, Inc. (Wallingford, Conn.). These feldspathic glass-ceramics comprise from about 40% to 50% of a discontinuous, fairly evenly dispersed, tetragonal potassium leucite phase, which imparts strength to the dental restoration. Leucite is a crystalline potassium aluminum silicate ($K_2O$ . $Al_2O_3$ . $4SiO_2$) which ordinarily has a tetragonal crystal structure at room temperature. Use of tetragonal leucite, also known as "low leucite", is described for reinforcement of feldspathic dental porcelains in U.S. Pat. No. 3,052,982 to Weinstein et al., U.S. Pat. No. 4,604,366 to Kacicz et al., U.S. Pat. No. 4,798,536 to Katz, and U.S. Pat. No. 5,614,330 to Panzera, the entire contents of the foregoing patents being incorporated herein by reference. While well-suited for their intended purposes, prior art porcelains for all-ceramic restorations are available in a limited range of maturing temperatures and CTEs, and contain leucite having at least some coarse-grained morphology, that is, a distribution of grain sizes wherein at least a fraction of the grains are greater than about 10 microns, or even greater than about 20 microns. Such coarse-grained leucite can wear away the opposing natural dentition in the mouth.

It has been disclosed in "Thermal Expansion Data XV. Complex Oxides with the Leucite Structure and Frameworks Based on Six-Membered Rings of Tetrahedra," *The American Mineralogist*, Vol. 33, September-October, pp1476–1489, 1968 by D. Taylor and C. M. Henderson and in "Effect of Ion-Exchange on the Microsturcture and Thermal Expansion Behavior of a Leucite-Reinforced Porcelain," *J Dent Res* 77(4):583–588, April, 1998 by I. L. Denry, J. A. Holloway, and S. F. Rosenstiel that tetragonal rubidium leucite exhibits highest expansion among the other forms of leucite in the temperature range of 25° C.–300° C. As a result, the average value of the thermal expansion measured from 25° C. to about 400° C. of rubidium-leucite based glass-ceramics is still higher than that of glass-ceramics comprising other leucites.

There accordingly remains a need in the art for high-strength porcelain systems wherein the maturing temperature is low enough to match that of commercially-available metal frameworks, including gold alloys and porcelain cores, and even more advantageously, wherein the CTE may be adjusted to match a range of metal substructure or all ceramic cores. There particularly remains a need for high-strength porcelain systems having low maturing temperatures, yet higher CTEs, and having a fine-grained leucite crystal structure for reducing wear of the opposing natural dentition. Such porcelains must further be simple and inexpensive to manufacture.

SUMMARY OF THE INVENTION

The above-described drawbacks and deficiencies of the prior art are alleviated by the low-fusing dental porcelain compositions of the present invention comprising a glassy matrix and tetragonal rubidium leucite (hereinafter referred to as "rubidium leucite") dispersed therein, and having maturing temperatures in the range from about 650° C. to about 800° C., more preferably in the range from about 690° C. to about 790° C. and most preferably in the range from about 730° C. to about 780° C., and CTEs in the range from about 13 to about 17, more preferably in the range from about 13.5 to about 16, and most preferably in the range from about 14 to about $16 \times 10^{-6}/°$ C. (measured from 25° C. to 400° C.). The rubidium leucite in accordance with the present invention is preferably both fine-grained (i.e., having average diameters of less than about 5 microns) and uniformly sized. The compositions are described in more detail below.

In one embodiment of the method of the present invention, a porcelain frit comprising fine grain sized rubidium leucite is combined with at least one frit having a very low maturing temperature of about 650° C. to about 700° C. in order to produce the porcelain of the present invention. In another embodiment of the method of the present invention, the fine grain sized rubidium leucite is crystallized from a single glassy frit in the initially amorphous glass by heat-treatment of this starting amorphous glass powder.

The porcelains in accordance with the present invention are especially suitable for use in dental restorations as overlay porcelains in combination with both dental alloys and leucite-reinforced core porcelains such as those available from Jeneric®/Pentron® under the trademark OPC®. The restorations thus produced are both aesthetic and forgiving to natural dentition, in that the presence of fine-grained leucite results in less wear of the opposing dentition.

BRIEF DESCRIPTION OF THE DRAWINGS

Features of the present invention are disclosed in the accompanying drawings, wherein.

DETAILED DESCRIPTION OF THE INVENTION

Figure 1:
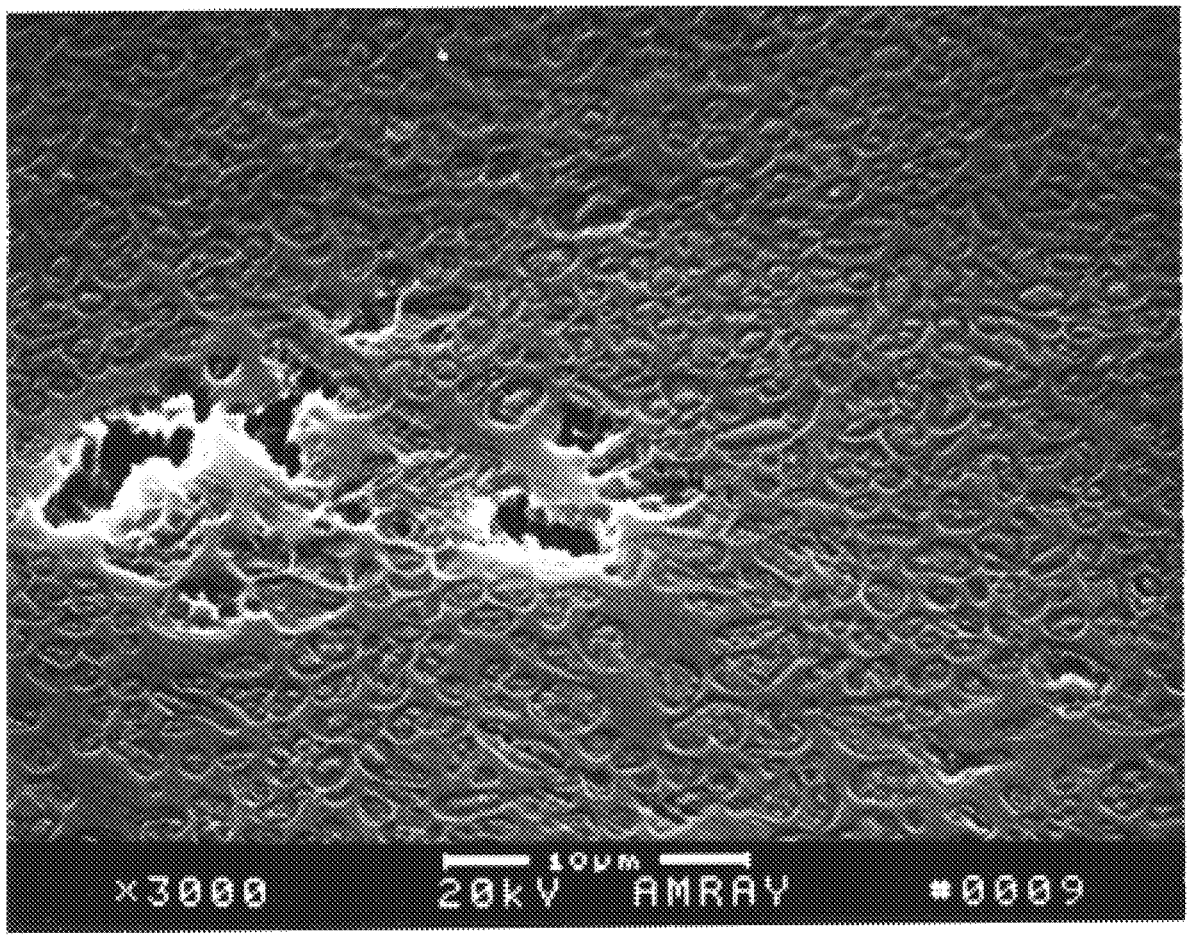
FIG. 1 is a microstructural view of the tetragonal rubidium leucite porcelain of the present invention at low magnification.

The present invention is directed to a low-fusing dental porcelain compositions of the present invention comprising a glassy matrix and rubidium leucite dispersed therein, and having maturing temperatures in the range from about 650° C. to about 800° C., more preferably in the range from about 690° C. to about 790° C. and most preferably in the range from about 730° C. to about 780° C., and CTEs in the range from about 13 to about 17, more preferably in the range from about 13.5 to about 16, and most preferably in the range from about 14 to about $16 \times 10^{-6}/°$ C. (measured from 25° C. to 400° C.). The rubidium leucite in accordance with the present invention is preferably both fine-grained (i.e., having average diameters of less than about 5 microns) and uniformly sized.

The rubidium leucite in accordance with the present invention is preferably both fine-grained and uniformly sized, in order to minimize wear to the opposing dentition. By "fine-grained" is meant leucite crystallites having average diameters of less than about five microns, preferably less than about three microns, and most preferably less than about one to two microns. Individual leucite grains having greater diameters may of course be present, but the presence of such grains is preferably minimized. As used herein, "diameters" refers to the longest single dimension of the crystallite, regardless of the shape of the crystallite.

The amount of leucite present in the glassy matrix is effective to achieve maturing temperatures in the range from about 650° C. to about 800° C. and coefficients of thermal expansion in the range from about 13 to about $17 \times 10^{-6}/°$ C. (measured from 25° C. to 400° C.), and is empirically determined by means known in the art, depending on the size and distribution of the tetragonal leucite, the composition of the glassy matrix, the desired maturing temperature and coefficient of thermal expansion, and the intended use of the porcelain (e.g., compatibility with the underlying core). Generally, the leucite is present in an amount in the range from about 3% to about 25% by weight of the total composition, and preferably in the range from about 5% to about 20% by weight of the total composition.

In one embodiment of the method of manufacture of the present invention, a first porcelain component comprising fine grain sized rubidium leucite having a thermal expansion of about $20 \times 10^{-6}/°$ C. (measured from 25° C. to 400° C.) is combined with at least one second porcelain component having a very low maturing temperature, for example in the range from about 650° C. to about 700° C. The composition of the first porcelain component and the at least one second porcelain component is such that combination of the first and second porcelain compositions yields the compositions given in Table 1 below. The higher the expansion of the crystalline phase which is present in the glass matrix, the lower the volume fraction of this phase that is necessary to attain the required value of thermal expansion of the resulting porcelain. The presence of the crystalline phase increases the fusion temperature of the resulting porcelain. Accordingly, the porcelain of the present invention attains high expansion with the smallest amount of crystalline phase present and a corresponding very small rise in fusion temperature. The advantages of the rubidium leucite porcelain of the present invention are truly realized when the glass transition temperature of the matrix glass is close to about 400° C. and the dispersion of the rubidium leucite phase is fine-grained and uniform to minimize thermal expansion mismatch stresses. In the present invention, the low fusing frit used to make the porcelain frit composition of the present invention is specifically developed to serve as matrix glass for the rubidium leucite crystalline phase and typically exhibits a glass transition temperature in the range of about 405° C. to about 440° C. and most preferably less than about 425° C. Examples of such low fusing frits are disclosed in commonly assigned copending application Ser. No. 09/113, 419 filed on Jul. 10, 1998 which is hereby incorporated by reference.

The rubidium leucite frit may be synthesized by means known in the art, for example by volume crystallization. Thus a mixture of powdered metal oxides or carbonates including the appropriated amount of an $Rb_2O$ precursor such as $Rb_2CO_3$ are blended in the appropriate proportions, for example by ball milling for one to three hours. Nucleation agents such as $P_2O_5$, Pt, combinations of MgO, ZnO, $TiO_2$ and the like are optionally added to the metal oxides and/or carbonates before blending in order to control nucleation density. The blended powders are then fused to form a glass melt, the glass is quenched (in water or by other means,) and then heated to an elevated temperature (e.g., 900° C.–1 100° C.) for approximately one to six hours, allowing the formation and growth of the crystalline leucite. An alternative method of crystallization heat-treatment of the amorphous glass in bulk or powder form is microwave processing. After leucite formation, the material is then quenched, crushed, and reduced to a fine powder. Volume crystallization is known in the art, being described for example in U.S. Pat. No. 4,455,383 to Panzera and U.S. Pat. No. 4,798,536 to Katz, the contents of which patents are incorporated by reference herein.

Alternatively, the powders are fused to form a glass, then directly cooled to the crystallization temperature without intermediate quenching.

Preferably, the rubidium leucite frit for the first porcelain component may be produced by the ion-exchange method described in application Ser. No. 08/960,684 filed Oct. 30, 1997, now U.S. Pat. No. 5,994,246 which is hereby incorporated by reference. Using this method, the rubidium leucite frit is fabricated from a low fusing frit having preferably $Al_2O_3$ in an amount greater than or equal to about 9% by weight and $K_2O$ in an amount greater than or equal to about 10% by weight. The ion exchange may be carried out for a time between about 8 and 48 hours at temperature in the range of about 430° C. to about 500° C. The temperature of the ion exchange is chosen just above the transition temperature of the starting glass. Following the ion-exchange, the powder is preferable rinsed five times to wash out the rubidium salt and crystallized at a temperature in the range of about 800° C. to about 1000° C. for a time period of about 0 to about 4 hours. An alternative method of crystallization heat-treatment of the amorphous glass in bulk or powder form is microwave processing.

As a further alternative, the rubidium leucite-containing porcelain component may be formed by surface crystallization of the precursor powder as set forth in copending application Ser. No. 60/062,345 filed Oct. 5, 1997 now non-provisional application Ser. No. 09/168,803 filed Oct. 8, 1998 which is hereby incorporated by reference. In this process, a mixture of powdered oxides and/or carbonates and/or other salts in the appropriate proportions (and optional nucleation agents) are blended, for example by ball milling for one to three hours. The powders are then melted to form a homogeneous glass melt, which is quenched in water or by other means. The quenched glass is then milled to a powder before subjecting the powder to heat treatment in order to crystallize rubidium leucite. An alternative method of crystallization heat-treatment of the amorphous glass in bulk or powder form is microwave processing. One example of a glassy powder used in the manufacture of a porcelain herein comprises about 64.6% $SiO_2$, about 6.0% $Al_2O_3$, about 11.0% $K_2O$, about 11.3% $Na_2O$, about 5% $Li_2O$, about 1.7% $B_2O_3$, about 2.1% CaO, about 0.7% MgO, and about 1.9% F.

Compositional ranges in weight percent for the rubidium leucite porcelains in accordance with the present invention are shown in the Table 1 below.

TABLE 1

| Component | Range (wt. %) |
|---|---|
| $SiO_2$ | 57–65 |
| $Al_2O_3$ | 6–12 |
| $K_2O$ | 7–15 |
| $Na_2O$ | 6–12 |
| $Li_2O$ | 0.3–3 |
| $B_2O_3$ | 0–5 |
| BaO | 0–2 |
| CaO | 0–3 |
| MgO | 0–4 |
| $Rb_2O$ | 0.5–10 |
| F | 0–2 |

TABLE 1-continued

| Component | Range (wt. %) |
|---|---|
| $P_2O_5$ | 0–3 |
| $CeO_2$ | 0–1 |
| $Sb_2O_3$ | 0–1 |
| Acidic flux[1] | 0.8–10 |
| Alkaline flux[2] | 6.3–15 |
| Additives[3] | 0–5 |

[1]$B_2O_3$ + F + $P_2O_5$
[2]$Li_2O$ + $Na_2O$
[3]Pigments, opacifying agents, fluorescing agents The presence of the acidic flux, that is, $B_2O_3$, $P_2O_5$ or F or their combination wherein $B_2O_3$+F+$P_2O_5$=0.8–10% by weight is necessary to attain the requisite crystallization parameters and/or to lower the maturing temperatures. Alkaline flux refers to the total quantity of $Li_2O$+$Na_2O$.

The porcelain in accordance with the present invention comprises or may further comprise other additives known in the art, such as opacifiers, pigments (e.g., chromates, vanadates, and manganates, and the like) and fluorescing agents (e.g., cerium oxide, 0.5–2% $Tb_2O_5$, 0–0.4% $Y_2O_3$, and the like).

The following Examples are representative of the porcelains of the present invention.

EXAMPLES

Figure 2:
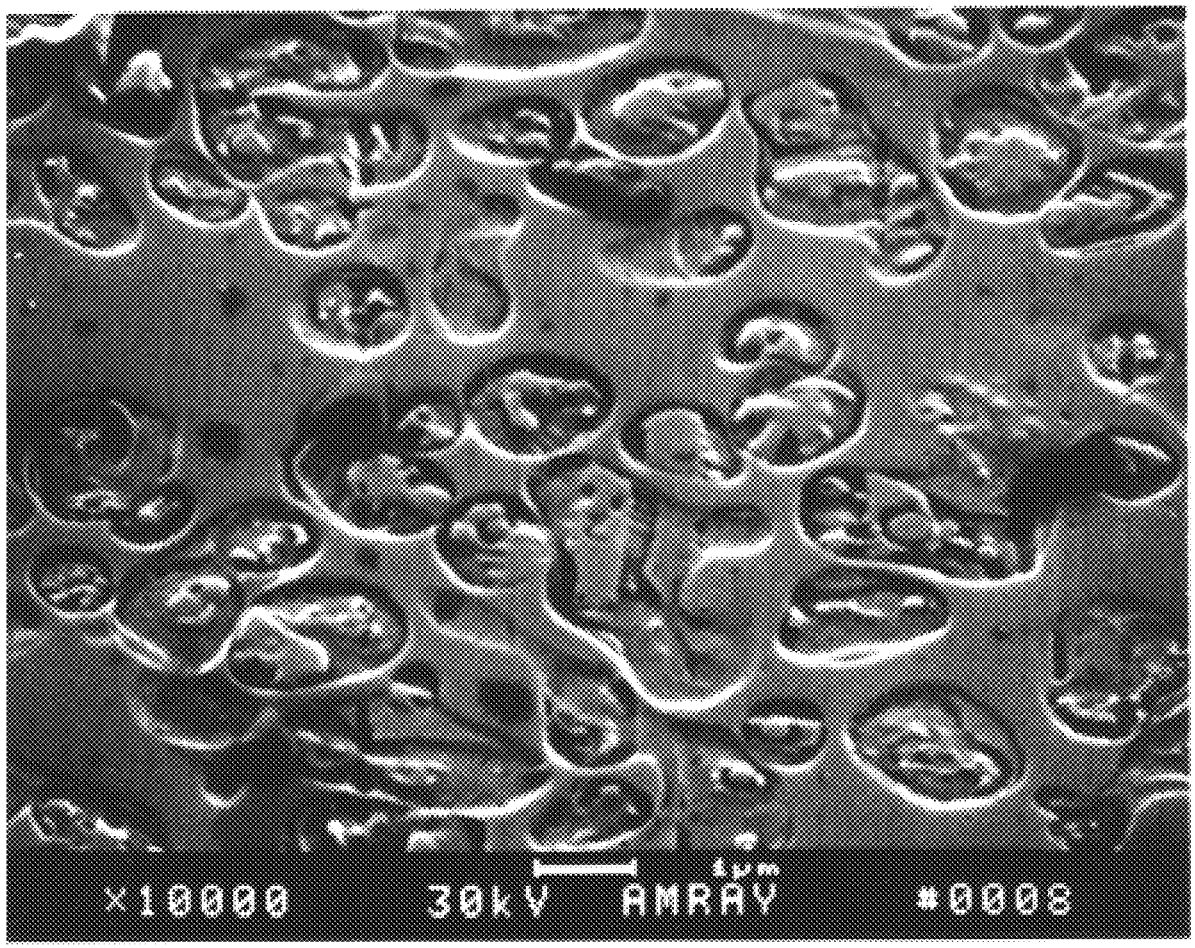
FIG. 2 is a microstructural view of the tetragonal rubidium leucite porcelain of the present invention at high magnification.
Figure 3:
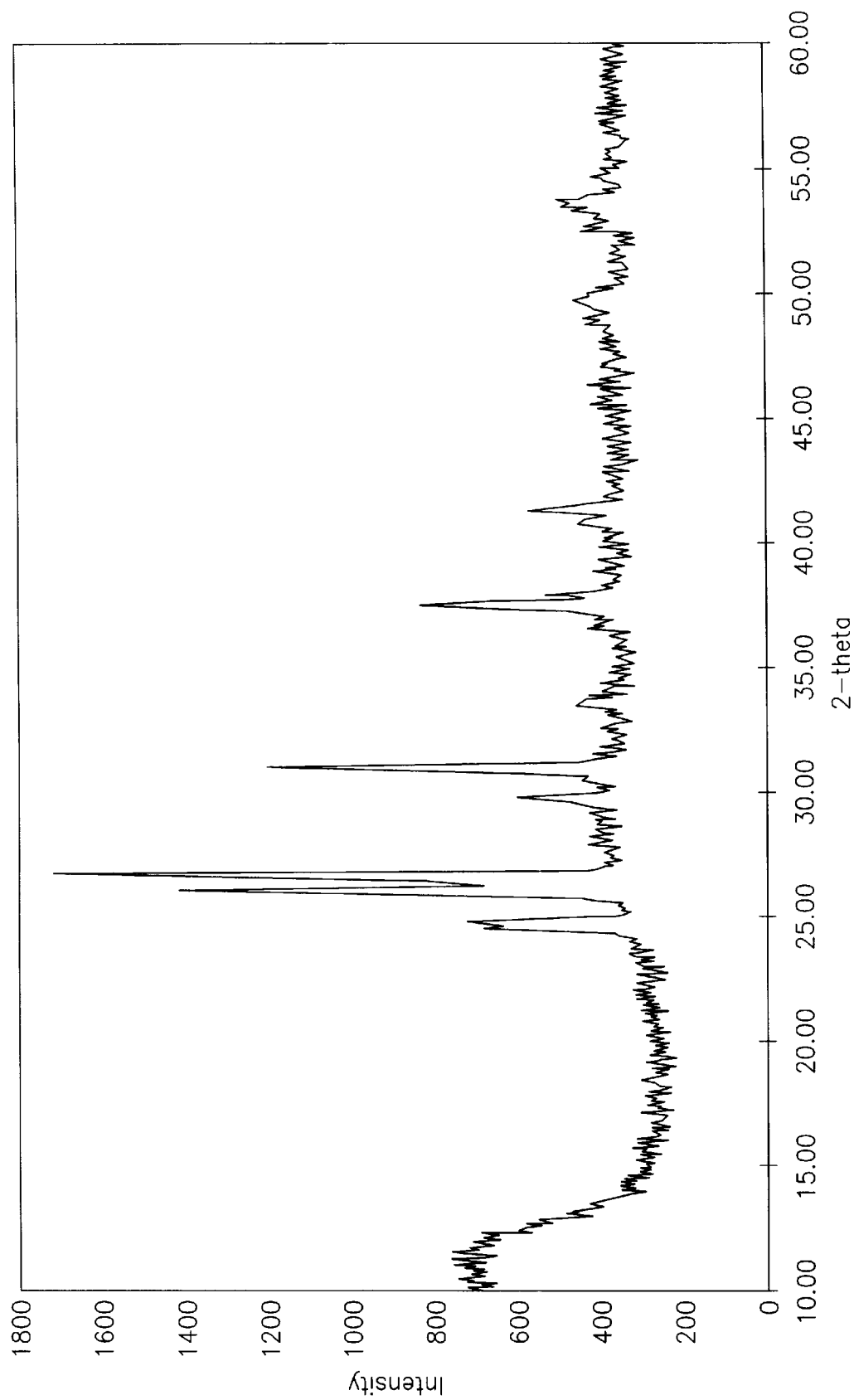
FIG. 3 is an X-ray diffraction diagram showing the patterns of tetragonal rubidium leucite porcelain of the present invention.

Porcelains of Examples 1 through 3 were prepared by admixing to the low-fusing component (Frit 1) a second frit (Frit 2) produced by ion exchange of the starting glass in a molten bath of $RbNO_3$ salt. The second component was chosen among suitable low-fusing frits having $Al_2O_3$ in an amount greater than or equal to about 9% by weight and $K_2O$ in an amount greater than or equal to about 10% by weight. The ion exchange was carried out for 48 hours at 450° C. The temperature of the ion exchange was chosen just above the transition temperature of the starting glass. Following the ion exchange, the powder was rinsed five times to wash out the rubidium salt and crystallized at 900° C. for four hours. The microstructure and x-ray diffraction pattern of the resulting porcelain comprising rubidium leucite is shown in FIGS. 1 through 3. Table 2 represents the compositional components of Frit 1, Frit 2A and Frit 2B used to make the resulting porcelains.

TABLE 2

| Components (wt. %) | Glass Frit 1 - low fusing component used in EXAMPLES 1, 2, & 3 | Glass Frit 2A used in EXAMPLE 1 and subjected to ion-exchange | Glass Frit 2B used in EXAMPLES 2 & 3 and subjected to ion-exchange |
|---|---|---|---|
| $SiO_2$ | 64.6 | 62.9 | 64.8 |
| $Al_2O_3$ | 6.0 | 9.7 | 10.0 |
| $K_2O$ | 11.0 | 15.3 | 14.7 |
| $Na_2O$ | 11.3 | 7.5 | 6.3 |
| $Li_2O$ | 1.5 | 1.2 | 1.1 |
| $B_2O_3$ | 1.7 | — | — |
| BaO | — | — | 0.1 |
| CaO | 2.1 | 1.1 | 0.7 |
| MgO | 0.7 | — | 1.4 |
| $Rb_2O$ | — | — | — |
| F | 1.9 | 1.8 | 1.5 |
| Glass Transition Temp. ° C. | 430 ± 10 | 440 ± 10 | 440 ± 10 |
| Softening Temp. ° C. | 500 ± 10 | 510 ± 10 | 510 ± 10 |
| Fusion Temp.-re ° C. (° F.) | 677 (1250) | 760 (1400) | 760 (1400) |
| CTE of Starting Glass (at 25–400° C.) | — | $11.2 \times 10^{-6}/°$ C. | — |
| CTE after Ion-Exhange & Crystallization (at 25–400° C.) | — | $19.4 \times 10^{-6}/°$ C. | — |

Table 3 shows properties of the rubidium leucite frits manufactured in the Examples in accordance with the present invention.

TABLE 3

|  | Rb-Leucite Porcelain Example 1 | Rb-Leucite Porcelain Example 2 | Rb-Leucite Porcelain Example 3 | Comparative Potassium Leucite Porcelain* |
|---|---|---|---|---|
| % glass frit 1: % Rb-Leucite frit 2 | 80:20 | 70:30 | 60:40 | — |
| Thermal Exp. (25° C.–400° C.) × $10^{-6}/°$ C. | 13.8 | 14.7 | 15.6 | 15.3 |
| Fusion Temp. ° C. | 690 | 730 | 780 | 857 |
| Approximate Rb-Leucite content volume percent | 10 | 15 | 20 | 35–40 |
| Leucite avg. grain size ($\mu$m) | 1–2 | 1–2 | 1–2 | 2 |

*Marketed under the name OPC ® Low Wear ™ by Jeneric/Pentron, Wallingford, CT.

The porcelain of Example 1 can be used as an add-on porcelain in combination with the porcelains of Examples 2 and 3. The porcelains of Examples 2 and 3 are compatible with OPC® core porcelains from Jeneric/Pentron Inc., Wallingford, Conn.

In one embodiment, the porcelain composition of the present invention is fused to a metal alloy framework or all-ceramic core to provide a coating thereon. Suitable alloys include those known in the art having a coefficient of thermal expansion in the range from about 13.2 to about $14.9 \times 10^{-6}/°$ C., or in the range from about 16 to about $17.5 \times 10^{-6}/°$ C.

Suitable all-ceramic cores include, but are not limited to cores available under the trade name OPC™ from Jeneric/Pentron, Wallingford, Conn.; under the trade name EMPRESS™, from Ivoclar; and under the trade name CERPRESS™, from the Dillon, Co., Cranston, R.I. Such restorations commonly have multiple porcelain layers in order to simulate natural teeth, and the porcelain of this invention may be used in any one or a combination of these layers, although it is preferably used as an overlayer. The porcelain layers are applied in the conventional manner, that is, in the form of a paste of the porcelain powder in water over the framework, shaping to the desired shape, and then firing.

In another embodiment, the porcelain is used to fabricate inlays, onlays, or veneers to replace amalgam, gold, or other porcelains. In this embodiment, the porcelain powder in accordance with the present invention is built on a refractory die in the form of an aqueous slurry, and then fired to an appropriate temperature to effect maturation and maturing of the porcelain.

While various descriptions of the present invention are described above, it should be understood that various features can be used singly or in any combination thereof. Therefore, this invention is not to be limited to only the specifically preferred embodiment depicted herein. Further, it should be understood that variations and modifications within the spirit and scope of the invention may occur to those skilled in the art to which the invention pertains. Accordingly, all expedient modifications ready attainable by one versed in the art from the disclosure set forth herein that are within the scope and spirit of the present invention are to by included as further embodiments of the present invention. The scope of the present invention is accordingly defined as set forth in the appended claims.

What is claimed is:

1. A composition for the manufacture of a dental porcelain, comprising
    a glassy matrix phase and a leucite crystallite phase, wherein the leucite phase comprises tetragonal rubidium leucite; and further wherein
    the porcelain has a maturing temperature in the range from about 650° C. to about 800° C. and a coefficient of thermal expansion in the range from about 13 to about $17 \times 10^{-6}/°$ C. (measured from 25° C. to 400° C.).

2. The composition of claim 1 wherein tetragonal rubidium leucite is present in the porcelain composition is an amount ranging from about 3 to about 25 wt %.

3. The composition of claim 1 wherein the average leucite crystallite diameter is less than about 5 microns.

4. The composition of claim 1, wherein the average leucite crystallite diameter is less than about 3 microns.

5. A composition for the manufacture of a dental porcelain, comprising

57–65% $SiO_2$, 6–12% $Al_2O_3$, 7–15% $K_2O$, 6–12% $Na_2O$, 0.3–3% $Li_2O$, 0–5% $B_2O_3$, 0–2% F, 0–3% $P_2O_5$ and 0.5–10% $Rb_2O$ by weight of the total composition, wherein the weight percent of $(F+B_2O_3+P_2O_5)$ is in the range from 0.8–10 and the weight percent of $(Li_2O+Na_2O)$ is in the range from 6.3–15;

wherein the porcelain comprises a glassy matrix phase and a leucite crystallite phase, wherein the leucite phase comprises tetragonal rubidium leucite; and further wherein the porcelain has a maturing temperature in the range from about 650° C. to about 800° C. and a coefficient of thermal expansion in the range from about 13 to about $17 \times 10^{-6}$/° C. (measured from 25° C. to 400° C.).

6. The composition of claim 5 further comprising 0–2% BaO, 0–3% CaO, 0–4% MgO, 0–1% $Sb_2O_5$, and 0–1% $CeO_2$.

7. The composition of claim 5 wherein rubidium-stabilized tetragonal leucite is present in the porcelain composition is an amount ranging from about 3 to about 25 wt %.

8. The composition of claim 5 wherein the average leucite crystallite diameter is less than about 5 microns.

9. The composition of claim 5 wherein the average leucite crystallite diameter is less than about 3 microns.

10. The composition of claim 5, wherein the average leucite crystallite diameter is between about 1 and about 2 microns.

11. A glassy powder for the manufacture of the porcelain of claim 1 comprising about 64.6% $SiO_2$, about 6.0% $Al_2O_3$, about 11.0% $K_2O$, about 11.3% $Na_2O$, about 1.5% $Li_2O$, about 1.7% $B_2O_3$, about 2.1% CaO, about 0.7% MgO, and about 1.9% F by weight of the total composition, wherein the porcelain is manufactured by surface crystallization of the glassy powder.

12. A dental restoration comprising the porcelain of claim 1.

13. A dental restoration comprising the porcelain of claim 5.

14. A method for making a dental porcelain restoration, comprising forming a dental porcelain powder from a dental composition comprising a glassy matrix phase and a leucite crystallite phase, wherein the leucite phase comprises tetragonal rubidium leucite; and further wherein the porcelain has a maturing temperature in the range from about 650° C. to about 800° C. and a coefficient of thermal expansion in the range from about 13 to about $17 \times 10^{-6}$/° C. (measured from 25° C. to 400° C.);

shaping the dental porcelain powder; and heating the shaped dental porcelain powder to between about 650° C. to about 800° C. to fuse the dental porcelain powder.

15. The method of claim 14 wherein the dental porcelain powder is fused to a ceramic core or a ceramic or metal framework.

16. A method for making a dental porcelain restoration, comprising:

forming a dental porcelain powder from a dental composition comprising 57–65% $SiO_2$, 6–12% $Al_2O_3$, 7–15% $K_2O$, 6–12% $Na_2O$, 0.3–3% $Li_2O$, 0–5% $B_2O_3$, 0–2% F, 0–3% $P_2O_5$ and 0.5–10% $Rb_2O$ by weight of the total composition, wherein the weight percent of $(F+B_2O_3+P_2O_5)$ is in the range from 0.8–10 and the weight percent of $(Li_2O+Na_2O)$ is in the range from 6.3–15;

wherein the porcelain comprises a glassy matrix phase and a leucite crystallite phase, wherein the leucite phase comprises tetragonal rubidium leucite; and further wherein the porcelain has a maturing temperature in the range from about 650° C. to about 800° C. and a coefficient of thermal expansion in the range from about 13 to about $17 \times 10^{-6}$/° C. (measured from 25° C. to 400° C.)

shaping the dental porcelain powder; and heating the shaped dental porcelain powder to between about 650° C. to about 800° C. to fuse the dental porcelain powder.

17. The method of claim 16 wherein the dental porcelain powder is fused to a ceramic core or a ceramic or metal framework.

18. The method of claim 16 wherein the powder further comprises

0–2% BaO, 0–3% CaO, 0–4% MgO, 0–1% $Sb_2O_5$, and 0–1% $CeO_2$.

* * * * *